(12) United States Patent
Giacobino et al.

(10) Patent No.: US 6,620,594 B1
(45) Date of Patent: Sep. 16, 2003

(54) UNCOUPLING PROTEIN HOMOLOGUE: UCP 3

(75) Inventors: Jean-Paul Giacobino, Genève (CH); Patrick Muzzin, Gland (CH); Olivier Boss, Boston, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/423,410

(22) PCT Filed: May 5, 1998

(86) PCT No.: PCT/EP98/02645

§ 371 (c)(1),
(2), (4) Date: Nov. 4, 1999

(87) PCT Pub. No.: WO98/50542

PCT Pub. Date: Nov. 12, 1998

(30) Foreign Application Priority Data

May 7, 1997 (CH) ................................................ 1072/97

(51) Int. Cl.[7] .......................... C12P 21/06; C12N 5/00; C12N 15/00; C07H 21/02; C07H 21/04
(52) U.S. Cl. .................... 435/69.1; 435/320.1; 435/325; 536/23.1; 536/23.5
(58) Field of Search ..................... 514/44, 2; 435/320.1, 435/325, 69.1; 536/23.1, 23.5; 530/350

(56) References Cited

FOREIGN PATENT DOCUMENTS

| WO | WO 96 05861 | 2/1996 |
|---|---|---|
| WO | WO98/39432 | 9/1998 |
| WO | WO98/45313 | 10/1998 |
| WO | WO98/45438 | 10/1998 |
| WO | WO98/52958 | 11/1998 |

OTHER PUBLICATIONS

Eck, et al., 1996. In Goodman & Gilman's The Pharmacological Basis of Therapeutics, Ninth edition, McGraw–Hill, New York, pp. 77–101.*

Alberts, et al., 1994. Molecular Biology of the Cell, Garland Publishing, New York, NY.*
Vidal–Puig, etal., Jun. 9, 1997. Biochem Biophys Res Com 235:79–82.*
Boss et al., FEBS LETT. vol. 408(1), pp 39–42 (1997).
Vidal–Puig et al., Biochem. Biophys. Res. Commun., vol. 235(1) pp 79–82 (1997).
Da–Wei Gong et al., Journal of Biological Chemistry, vol. 272, No. 39, pp. 24129–24132.
Fleury et al., UCP2, Emhum Database entry HSU76367, Accession No. U76367: (1997).
Hillier et al., Ernest Database entry Hsaa98452, Accession No. AA192136: (1997).
Marra et al., EMEST Database entry Mmaa8362, Accession No. AA108362 (1996).
Millet et al., J. Clin. Invest, vol. 100, No. 11, pp. 2665–2670 (1997).
Liu et al., Gene 207, pp. 1–7 (1998).
Boss et al., Eur. J. Endocrinal. (in press) pp. 1–26.

* cited by examiner

Primary Examiner—Jeffrey Fredman
Assistant Examiner—Samesh Kaushai
(74) Attorney, Agent, or Firm—Gregory D. Ferraro

(57) ABSTRACT

The present invention relates to the cloned genes which code for uncoupling proteins controlling thermogenesis in human skeletal muscle and heart. A further aspect of the present invention relates to the use of the said genes for correcting dysfunctions of thermogenesis in human skeletal muscle and heart.

The present invention makes it possible to exploit novel therapeutic (or preventive) methods for disorders such as obesity or cachexia. As a result of the identification and isolation of the genes coding for $UCP3_L$ and $UCP3_S$, it is, in effect, possible to develop medicaments which act on the basis of a correction, by gene therapy or by antisense oligonucleotides relating to the sequence of the gene in question or to one of its fragments, of a lack or an excess of UCP3.

5 Claims, No Drawings

UNCOUPLING PROTEIN HOMOLOGUE: UCP 3

This application is the National Stage of International Application No. PCT/EP98/02645, filed on May 5, 1998.

The present invention relates to a cloned gene which codes for an uncoupling protein (UCP3$_L$) which controls thermogenesis in human skeletal muscle and heart.

The present invention also relates to a cloned gene which codes for an uncoupling protein (UCP3$_S$), also controlling thermogenesis in human skeletal muscle and heart.

A further aspect of the present invention relates to the use of the said cloned genes for correcting dysfunctions of thermogenesis in human skeletal muscle and heart.

A dysfunction of thermogenesis can induce disorders such as obesity or cachexia.

Obesity is characterized by an excess of adipose mass which can represent more than 30% of the bodyweight. The incidence of this disturbance of energy balance is constantly increasing in industrialized countries. Preventing the development of obesity, or treating it, would enable the complications associated with this pathology, namely cardiovascular diseases, hypertension and type II diabetes, to be avoided.

In some special cases, the control of thermogenesis could also prove useful. In man, weight loss following a slimming diet induces a saving of energy by the body. On resumption of normal feeding, the energy expenditure remains reduced until the body has recovered the adipose mass and the lean mass which it has lost previously. This decrease in energy expenditure often leads to an excess weight regain. A similar problem is encountered in endurance athletes as soon as they stop training. In effect, in a trained person, the energy expenditure is decreased relative to that of a sedentary person. This energy saving is responsible for a substantial weight gain (most especially of fat) after chronic physical activity has been stopped.

Cachexia is a metabolic situation in which the energy expenditure exceeds the food intake. Its main causes are underfeeding (e.g. anorexia nervosa), cancer, infectious diseases including AIDS and a state of shock. The decrease in adipose and muscle masses can threaten the individual's survival.

The energy expenditure is increased in the mitochondria by uncoupling of the oxidative phosphorylations. The oxidations induce the exit of protons (H$^+$) from the mitochondrion, creating a proton gradient which, as it dissipates, permits the synthesis of ATP. Uncoupling can be induced by chemical compounds such as 2,4-dinitrophenol (DNP) and by other acidic aromatic compounds. These substances carry H$^+$ from the outside to the inside of the inner mitochondrial membrane. In the presence of these uncoupling agents, the oxidation of NADH takes place normally, but ATP is not formed by the mitochondrial ATP synthetase since the proton gradient is dissipated.

Brown adipose tissue (BAT), which is very rich in mitochondria, is specialized in this process of thermogenesis. The inner membrane of its mitochondria contains a large amount of an uncoupling protein (UCP) which enables protons to return from the outside to the inside of the mitochondrion. In essence, the uncoupling protein produces heat by short-circuiting the battery of mitochondrial protons. In spite of its tissue specificity, UCP is a member of the mitochondrial carrier family, which includes the ATP/ADP, phosphate and 2-oxoglutarate/malate carriers, in particular. In contrast to the ATP/ADP carrier, which is a constitutive carrier, UCP is subjected to substantial regulatory processes (M. Klingenberg, *J. Bioenerg. Biomembr.* 25, 447 (1993)). Its activity is decreased by purine di- or triphosphate nucleotides and increased by fatty acids (J. Nedergaard, B. Cannon, in *New Comprehensive Biochemistry* (*Bioenergetics*) L. Ernster, Ed (Elsevier Science, Stockholm, 1992), vol. 23, 385).

The uncoupling of oxidative phosphorylation is very useful from a biological standpoint; it is a means for BAT to generate heat in order to maintain a physiological temperature in the newborn offspring of some animals (including man) and in the mammals of the cold regions.

The human UCP gene is localized at 4q31; it consists of six exons and codes for a protein of 307 amino acids with no targeting presequence signal. Like other mitochondrial carriers, UCP is inserted into the mitochondrial membrane by six hydrophobic α-helical domains, each encoded by a portion of the six exons (L. P. Kozak et al., *J. Biol. Chem.* 263, 12274 (1988)). Its polypeptide chain consists of three related sequences in tandem of approximately 100 amino acids, each encoded by two exons and corresponding to two transmembrane domains (F. Bouillaud et al., *Biochem. Biophys. Res. Commun.* 157, 783 (1988)). Topological studies suggest that the amino- and carboxy-terminal ends of UCP are oriented towards the cytosol side of the inner mitochondrial membrane (B. Miroux et al., *EMBO J.* 12, 3739 (1993)). Furthermore, J. Nedergaard et al. (*New Comprehensive Biochemistry* (*Bioenergetics*) L. Ernster, Ed. (Elsevier Science, Stockholm, 1992), vol. 23, 385) and D. Ricquier et al. (*FASEB J.* 5, 2237 (1991)) have shown that the expression of UCP is increased at transcriptional level by noradrenaline. This effect is mediated by stimulation of the three subtypes of β-adrenoceptors (β$_1$, β$_2$ and β$_3$) and of the α$_1$-adrenoceptor.

However, M. E. J. Lean et al. (*Brown Adipose Tissue* P. Trayhurn, D. G. Nicholls, Eds, (Edward Arnold, London, 1986), 339) have shown that, in man, the BAT, expressing UCP, present in newborn infants decreases considerably in adults. Hence, under physiological conditions, BAT cannot play an important part in non-shivering thermogenesis in man.

On the other hand, L. Simonsen et al. (*Int. J. Obes.* 17, S47 (1993)) have determined that, in man, skeletal muscle contributes to the extent of approximately 40% to adrenaline-induced body thermogenesis. Studies performed on rats (P. L. Thurlby et al., *Can. J. Physiol. Pharmacol.* 64, 1111 (1986); I. Nagase et al., *J. Clin. Invest.* 97, 2898 (1996)) suggest that adrenaline-induced thermogenesis in human skeletal muscle (L. Simonsen et al., *Int. J. Obes.* 17, S47 (1993)) could be mediated by a muscle UCP.

In the search for homologues of UCP in human skeletal muscle, we have screened a library of human skeletal muscle cDNA, and three clones (UCP2, UCP3$_L$ and UCP3$_S$) have been isolated. Whereas UCP2 mRNA has been found in all human tissues studied, as has also been described by Fleury et al. (*Nature Genet.* 15, 269 (1997)), UCP3 has proved to be very specific to human skeletal muscle. This new member of the UCP family, with a strong specificity of expression in skeletal muscle, is involved in the control of oxidative phosphorylations in man.

The characterization of the genes coding for UCP3$_L$ and UCP3$_S$ in terms of nucleotides and of amino acids is described here for the first time.

One aspect of the present invention is hence a DNA fragment, characterized in that it contains the nucleotide sequence depicted in SEQ ID NO 3, the said DNA fragment coding for an uncoupling protein (UCP3$_L$) which is characterized by the amino acid sequence depicted in SEQ ID NO 4, or in that it contains a homologous sequence coding for the same amino acid sequence. Preferably, the chosen DNA fragment originates from human skeletal muscle.

Another aspect of the present invention is a DNA fragment, characterized in that it contains the nucleotide sequence depicted in SEQ ID NO 5, the said DNA fragment coding for an uncoupling protein (UCP3$_S$) possessing the amino acid sequence depicted in SEQ ID NO 6, or in that it contains a homologous sequence coding for the same amino acid sequence. Preferably, the chosen DNA fragment originates from human skeletal muscle.

One subject of the present invention is an uncoupling protein, characterized in that it comprises the amino acid sequence depicted in SEQ ID NO 4.

Another subject of the present invention is an uncoupling protein, characterized in that it comprises the amino acid sequence depicted in SEQ ID NO 6.

Furthermore, the present invention sets out to provide a recombinant DNA fragment which contains one of the nucleotide sequences depicted in SEQ ID NO 3 or NO 5, or one of their homologous sequences.

Another subject of the present invention provides a DNA molecule, characterized in that it comprises a cloning vector into which one of the said DNA sequences is inserted. Preferably, this cloning vector is a plasmid or a phagemid.

Another subject of the present invention is a recombinant DNA molecule, characterized in that it consists of the nucleotide sequence depicted in SEQ ID NO:3, inserted into the vector pBluescript SK⁻. This recombinant DNA molecule is deposited with the American Type Culture Collection, 12301 Parklawn Drive, Rockville, Md. 20852 USA (ATCC Designation NO 97999—date of deposition: Apr. 25, 1997).

Another subject of the present invention is a recombinant DNA molecule, characterized in that it consists of the nucleotide sequence depicted in SEQ ID NO:5, inserted into the vector pBluescript SK⁻. This recombinant DNA molecule is deposited with the American Type Culture Collection, 12301 Parklawn Drive, Rockville, Md. 20852 USA (ATCC Designation NO 209000—date of deposition: Apr. 25, 1997).

Another subject of the present invention is a microorganism selected from bacteria, yeasts and mammalian cells, characterized in that it contains one of the said recombinant DNA molecules. Preferably, the chosen microorganism is an XL1-Blue MRF' bacterium (*E. coli*).

Another aspect of the present invention relates to a pharmaceutical formulation for correcting a lack of UCP3 by gene therapy, which comprises the gene described in SEQ ID NO 3 or NO 5 and a suitable pharmaceutical vehicle. The said gene is preferably contained in a vector chosen from adenoviruses, retroviruses, adeno-associated viruses, herpesvirus, liposomes or DNA plasmids.

Construction of the adenoviral vector and production of the recombinant adenovirus may be accomplished using standard techniques (Graham et al., *Method in Molecular Biology*, 1991, Vol. 7, chap. 11, Murray, E. J., Ed., The Humana Press, Inc., Clifton, N.J.; Zabner et al., *Cell*, 75, 207–216 (1993); Crystal, et al., *Nature Genetics*, 8, 42–51 (1994)).

Construction of the retroviral vector and production of the recombinant retrovirus may be accomplished using standard techniques (Miller, A. D. et al., *Meth. Enzymol.*, 217, 581–599 (1993); Blaese et al., *Human Gene Therapy*, 1, 331–362, (1990)).

Construction of the adeno-associated viral vector and production of the recombinant adeno-associated virus may be accomplished using standard techniques (Muzyczka, *Curr. Top. Microbiol. Immunol.*, 158, 97–129 (1992)).

Construction of the herpesviral vector and production of the recombinant herpesvirus may be accomplished using standard techniques (Glorioso et al., *Semin. Virol.*, 3, 265–276 (1992)).

Production of the liposome containing the UCP3 gene may be accomplished using standard techniques (Kirby et al., *Biotechnology*, 2, 979–984 (1984); Felgner et al., *Proc Natl Acad Sci USA*, 84, 7413–7417 (1987); Gregoriadis et al., *J. Drug Targeting*, 3, 467–475 (1966)).

Construction of the DNA plasmid and production of the recombinant DNA plasmid may be accomplished using standard techniques (Lee et al., *Cancer Res.*, 54, 3325–3328 (1994)). The functionality of the recombinant retroviral vector, the recombinant adeno-associated viral vector, the recombinant herpesviral vector, the UCP3 gene encapsidated in the liposome, and the recombinant DNA plasmid may, in each case, be evaluated by the expression of UCP3 in transfected cells and by the presence of the UCP3 protein, using the northern blot technique (Sambrook, et al., *Molecular Cloning*, 1989, Nolan, C., Ed., Cold Spring Harbor Laboratory Press, Cold Spring Harbor, N.Y.) and the western blot technique (Sambrook, et al., *Molecular Cloning*, 1989, Nolan, C., Ed., Cold Spring Harbor Laboratory Press, Cold Spring Harbor, N.Y.), respectively.

In addition, a subject of the present invention is a medicament for correcting an excess of UCP3, which comprises as active principle antisense oligonucleotides relating to fragments of the sequences of UCP3$_L$ and of UCP3$_S$.

The present invention thus makes it possible to exploit novel therapeutic (or preventive) methods for disorders of the abovementioned type. As a result of the identification and isolation of the genes coding for UCP3$_L$ and UCP3$_S$, it is, in effect, possible to develop medicaments which act on the basis of a correction, by gene therapy or by antisense oligonucleotides relating to the sequence of the gene in question or to one of its fragments, of a lack or an excess of UCP3.

Gene therapy is indicated in the case of a dysfunction of UCP3 due to one or more mutations of the UCP3 gene. In this case, there is transfer of a normal gene into the UCP3-deficient cells using an appropriate vector. Preferably, the vector is chosen from adenoviruses, retroviruses, adeno-associated viruses, herpesvirus, liposomes or plasmids. In this case the UCP3 gene is under the control of an exogenous promoter. The administration of antisense oligonucleotides is specifically indicated for cases where the UCP3 level and/or the activity of the UCP3 might be excessive.

By means of the present invention, it will, in addition, be possible to develop medicaments which act on the modification of the activity and/or on the level of expression of endogenous UCP3.

Intervention in respect of the modification of endogenous UCP3 activity could be especially indicated for inducing a loss of bodyweight (loss of adipose mass and maintenance of the lean mass) in all types of obesity by promoting the dissipation of energy. It was shown that the level of UCP3 mRNA in skeletal muscle is lower in fa/fa obese rats than in lean Fa/? rats (O. Boss et al., *J Biol. Chem.* 273, 5 (1998)). The same intervention could also be applied for preventing an excessive weight regain following a restrictive food diet or after ceasing a physical training programme. It was shown that food restriction induces a decrease in the UCP3 gene expression in skeletal muscle (O. Boss et al., *J. Biol. Chem.* 273, 5 (1998)), and this expression remains very low for a prolonged period of time during refeeding (D. W. Gong et al., *J. Biol. Chem.* 272, 24129 (1997)). It was also reported that endurance exercise training induces a decrease in the UCP3 gene expression in skeletal muscle (O. Boss et al., *FASEB J* 12, 335 (1998)). The same intervention could be applied for preventing and treating type II diabetes by improving the sensitivity to insulin, and for preventing hypertension. The same intervention could also be applied for increasing muscle mass in states of cachexia. It could also be applied for the treatment of insufficiencies or disturbances of cardiac rhythm due to a dysfunction of UCP3, or for the treatment of neuromuscular diseases due to a dysfunction of UCP3. The UCP3 activators or inhibitors could be administered enterally or parenterally.

Modification of the level of expression of endogenous UCP3 would also be indicated for the abovementioned cases; intervention could take place using activators or inhibitors of UCP3 expression. These substances could be administered enterally or parenterally. Possible candidates for modulating the expression would be activators or inhibitors of transcription factors specific to UCP3, or hormones. It was shown that thyroid hormones (T3), glucocorticoids (dexamethasone), β-adrenergic receptor agonists (Ro 16-8714), leptin, and fatty acids induce an increase in the UCP3 gene expression in skeletal muscle (D. W. Gong et al., *J. Biol. Chem.* 272, 24129 (1997), S. Larkin et al., *Biochem. Biophys. Res. Com.* 240, 222 (1997), O. Boss et al., Unpublished observations (1997), I. Cusin et al., *Diabetes*, (in press, 1998), D. S. Weigle et al., *Diabetes* 47, 298 (1998)). On the other hand hypothyroidism was shown to be associated with a lower level of UCP3 mRNA in skeletal muscle (D. W. Gong et al., *J. Biol. Chem.* 272, 24129 (1997)).

The construction of cells containing the $UCP3_L$ and/or $UCP3_S$ gene may be accomplished using standard techniques (*Methods in Molecular Biology*, 1991, Vol. 7, chap. 2–5, Murray, E. J., Ed., The Humana Press, Inc., Clffton, N.J.; Sambrook, et al., *Molecular Cloning*, 1989, Nolan, C., Ed., Cold Spring Harbor Laboratory Press, Cold Spring Harbor, N.Y.). The expression of the UCP3 gene in the transfected cells may be evaluated by the northern blot technique and western blot technique. Cultured $C_2C_{12}$ mouse myoblasts have been transfected with the human $UCP3_L$ cDNA, and the expression of UCP3 has been evaluated by the northern blot technique (O. Boss et al., *J. Biol. Chem.* 273, 5 (1998)). The functionality of the UCP3 protein may be evaluated by measuring the respiration on isolated cells expressing the UCP3 protein or mitochondrial fractions (*Methods in Enzymology*, Vol. 10, chap. 14, 86–94 (1967)) containing the UCP3 protein. The measurements of oxygen consumption are performed by polarography (*Methods in Enzymology*, Vol. 10, chap. 7, 41–48 (1967)) using a Clark electrode. It is also possible to evaluate the activity of the UCP3 protein using cytofluorometric methods for measuring the mitochondrial membrane potential (*Methods in Enzymology*, Vol. 260, chap. 29, 406–417, chap. 31, 428–447 (1985)). Fluorescent compounds are used to analyse the changes in mitochondrial membrane potential. With the help of a cytofluorometric method the UCP3 has been shown to decrease the mitochondrial membrane potential of $C_2C_{12}$ mouse myoblasts that have been transfected with the human $UCP3_L$ cDNA (O. Boss et al., *J. Biol. Chem.* 273, 5 (1998)). A screening of medicaments capable of modifying UCP3 activity could be accomplished by measuring the oxygen consumption and/or the mitochondrial membrane potential on isolated cells and/or mitochondria containing the UCP3 protein. Medicaments that modify the activity of the UCP3 protein could then be tested in vivo on animal models displaying an excess or otherwise a defect of UCP3 activity.

Antibodies, or their derivatives, against UCP3 or UCP3 fragments could be developed in order to enable the UCP3 level to be measured in biological samples for diagnostic purposes. These antibodies could serve to target substances in proximity to UCP3 with a view to modifying UCP3 activity.

In addition, transgenic animals expressing an excess of normal or modified UCP3, and animals with an invalidation of the UCP3 (knock-out), could be created in order to permit an evaluation of the biological role of UCP3 and/or the effects of a change in activity and/or in level and/or in structure of the UCP3 on the animal's biology. The transgenic animals could also be used to screen or test substances that modify UCP3 expression and/or activity.

Other advantages of the present invention will become manifest on reading the description which follows.

The brief description of the figures as disclosed in O. Boss et al., *FEBS Lett.* 408, 39 (1997) are hereby incorporated by reference into the specification and any discussion herein of Figures is referring to FIGS. 1 and 2 of the Boss et al. document.

Total RNAs of rat tibialis anterior muscle and interscapular BAT were purified by the method described by Chomczynski et al. (*Anal. Biochem.* 162, 156 (1987)). 1–2 µg of each RNA were reverse transcribed using oligo$(dT)_{16}$ primers and Moloney murine leukaemia virus (M-MLV) reverse transcriptase (Gibco BRL, New York, N.Y.). Briefly, the RNA was mixed with 1.5 µl (150 ng) of oligo$(dT)_{15}$ in a total volume of 17.5 µl. The mixture was heated to 70° C. for 10 min and cooled on ice. After a brief centrifugation, the RNA was reverse transcribed for one hour at 41° C. (total volume 25 µl). The aliquots of first strand cDNA were stored at −20° C. until use. The polymerase chain reaction was performed in a Perkin Elmer DNA Thermal Cycler 480 (Perkin Elmer, Lausanne, Switzerland). The first strand cDNA (2 µl) was amplified in a total volume of 50 µl in the presence of oligonucleotide primers corresponding, on rat UCP, to domains conserved between the species: positions 279–298: CTGGACACCGCCAAAGTCCG (UCPRF) (SEQ ID NO:1) positions 1021–1044: AGCACACAAACATGAT-GACGTTCC (UCPRR) (SEQ ID NO:2) on GenBank Accession M11814. A unique fragment of similar size was obtained in the BAT and in the tibialis anterior muscle. The sequence of the BAT PCR product was identical to that of rat UCP, whereas the sequence of the tibialis anterior muscle PCR product was 60% identical to that of rat UCP. This fragment, called rat atypical UCP cDNA, was radioactively labelled with the nucleotide [α-$^{32}$P]dCTP and used as probe to screen a human skeletal muscle cDNA library (Stratagene, #936215, La Jolla, Calif.).

Approximately one million phages of the human skeletal muscle cDNA library (Human Muscle cDNA Library Lambda ZAPS® II Vector, #936215, Stratagene) were screened using the abovementioned rat atypical UCP cDNA probe according to the manufacturer's instructions (Mar. 8, 1994). The screening led to the isolation of ten positive clones. Among these, three different categories were purified using a kit for plasmids (Qiagen, Santa Clarita, Calif.) according to the manufacturer's instructions, and sequenced with an ABI373A automatic sequencer according to the standard protocols using the oligonucleotide primers M13-20 and T3 and others specific to the gene, until the sequence was determined on both strands. The predicted peptide sequences of these three clones, which contain 309, 312 and 275 amino acids, are illustrated in FIG. 1 (O. Boss et al., *FEBS Lett.* 408, 39 (1997)). The protein of 309 amino acids is UCP2 (GenBank Accession U82819), which was also isolated by Fleury et al., (*Nature Genet.* 15, 269 (1997)). The other two proteins have their first 275 amino acids in common, suggesting that they are isoforms. It was shown that these isoforms arise from alternative splicing of the UCP3 RNA (G. Solanes et al., *J. Biol. Chem.* 272, 25433 (1997)). They have a 56% and 73% identity of amino acids with human UCP and UCP2, respectively, and are hence considered to be new proteins, called UCP3 long and short forms, $UCP3_L$ and $UCP3_S$, respectively (GenBank Accessions U84763 and U82818). Like the other mitochondrial carriers, UCP2 and $UCP3_L$ contain six potential transmembrane domains (FIG. 1). The potential purine nucleotide binding domain extends from nucleotides 276 to 298 in UCP2 and from 279 to 301 in $UCP3_L$. $UCP3_S$ does not have the sixth potential transmembrane region, or the purine nucleotide binding domain involved in the control of the uncoupling activity of UCP (F. Bouillaud et al., *EMBO J.* 13, 1990 (1994)).

The binding of guanosine diphosphate (GDP) to UCP induces a conformational change causing an inhibition of the permeability of $H^+$ and $Cl^-$ ions (J. Nedergaard et al., in *New Comprehensive Biochemistry* (*Bioenergetics*) L. Ernster, Ed. (Elsevier Science, Stockholm, 1992), vol. 23, 385). Thus, $UCP3_S$ appears to exert its biological activity without control by GDP. As illustrated in FIG. 1, other structural features of the mitochondrial carriers are observed in UCP2, as welt as in $UCP3_L$ and $UCP3_S$: the three signature domains of the mitochondrial energy transfer proteins (A. Bairoch, *Nucleic Acids Res.* 21, 3097 (1993)), which can be identified at the downstream border of the first, third and fifth potential transmembrane domains (O. Boss et al., *FEBS Lett.* 408, 39 (1997)), and the fourteen conserved residues of the mitochondrial carriers (F. Palmieri, *FEBS Lett.* 346, 48 (1994)).

UCP2 and UCP3 have the strongest homology (with respect to amino acids and nucleotides) with UCP, compared to the other members of tne mitochondrial carrier family (O. Boss et al., *FEBS Lett.* 408, 39 (1997)). In fact, their identity with UCP is 55% and 56%, respectively, whereas that with the most homologous mitochondrial protein, the 2-oxoglutarate/malate carrier, is 32%. UCP2 and UCP3 should hence belong to the UCP family. In fact, Fleury et al., (*Nature Genet.* 15, 269 (1997)) and Gimeno et al. (*Diabetes* 46, 900 (1997)) have shown that UCP2 has mitochondrial uncoupling properties when it is expressed in yeast, whereas Gong et al. (*J. Biol. Chem.* 272, 24129 (1997)) and Boss et al. (*J. Biol. Chem.* 273, 5 (1998)) have shown that UCP3 has mitochondrial uncoupling properties when it is expressed in yeast or in $C_2C_{12}$ mouse myoblasts, respectively.

Comparison of the Distribution of UCP2 and UCP3 in Human and Rat Tissues. (O. Boss et al., *FEBS Lett.* 408, 39 (1997))

The tissue distribution of UCP3 was compared with that of UCP2 by northern blotting. For this purpose, the following materials were made available:

Samples of Human Tissues

The poly(A) RNA membrane of numerous human tissues (#7760-1) is obtained from Clontech Laboratories Inc. (Palo Alto, Calif.). Fragments of abdominal white adipose tissue (10 to 40 g) or of abdominal skeletal muscle (800 mg) were obtained during intra-abdominal surgical operations. Pieces of perirenal brown adipose tissue weighing approximately 1.5 g were obtained during renal surgical operations on children (average age: 3 months). The project was approved by the Ethical Committee of the Department of Surgery, Faculty of Medicine, University of Geneva.

Samples of Rat Tissues

Seven-week-old male Sprague-Dawley rats fed ad libitum with a standard laboratory feed were kept in individual cages with a day-night cycle of 12 h. They were sacrificed by cervical dislocation. All the experiments were performed in accordance with the instructions of our establishment.

Northern Analysis

The total RNAs (10–20 μg) were subjected to eiectrophoresis in a 1.2% agarose gel containing formaldehyde, as described by Lehrach et al., (*Biochemistry* 16, 4743 (1977)), and transferred onto a nylon membrane (Electran Nylon Blotting Membrane, BDH Laboratory Supplies, Poole, United Kingdom) with a vacuum apparatus (Stratagene, La Jolla, Calif.). The probes were labelled using random primers (Megaprime DNA Labelling System, Amersham, Bucks, United Kingdom) with [α-$^{32}$P]dCTP (3000 Ci/mmol) (Amersham, Bucks, United Kingdom) at a specific activity of approximately $1 \times 10^9$ dpm/μg DNA. The RNA membranes were hybridized for 2 h at 65° C. in QuikHyb (Stratagene, La Jolla, Calif.), and then washed in a 2×SSC (1×SSC is 150 mM NaCl, 15 mM sodium citrate, pH 7.0)/0.1% SDS solution at 50° C. for twice 5 minutes and in 0.1×SSC/0.1% SDS at 50° C. for 5 minutes. The membranes were exposed to Hyperfilm ECL films (Amersham, Bucks, United Kingdom) at −80° C. with intensifying screens. The standard RNAs used are the Kb RNA Ladder from Gibco BRL (New York, N.Y.).

UCP2 signal in ubiquitously expressed in tissues. UCP2 is expressed at the highest level in BAT>white adipose tissue>skeletal muscle. In contrast, the expression of UCP3 (signal at 2.3 kb) is limited to the skeletal muscle and the heart. UCP3 is 10 times more strongly expressed in skeletal muscle. Direct comparison of the northern blots hybridized with the UCP2 and UCP3 probes showed that UCP3 is much more strongly expressed in skeletal muscle that UCP2. Probes specific for the long form or the short form of UCP3 showed that both forms give the same signal at 2.3 kb, and quantification of the intensity of the signal showed that both forms are expressed at a similar level in human skeletal muscle (O. Boss et al., *FEBS Lett.* 408, 39 (1997)).

The tissue distribution of UCP2 mRNA and UCP3 mRNA was also studied in rats using the rat atypical UCP cDNA probe, which hybridizes with the three species of rat UCP, UCP2 and UCP3 (O. Boss et al., *FEBS Lett.* 408, 39 (1997)). A major difference from human UCP2 is its high level of expression in heart. UCP3 is expressed at the highest level in BAT, at a high level in the tensor fascia latae (fast-twitch, glycolytic), tibialis anterior (fast-twitch, oxidative-glycolytic) and gastrocnemius (mixed) muscles and at a lower level in the soleus muscle (slow-twitch, oxidative). This suggests that UCP3 is more strongly expressed in the glycolytic than in the oxidative skeletal muscles. In rats, UCP3 was also detected, though at a much lower level, in the heart and kidney, and occasionally in the white adipose tissue.

The UCP3 signal is a doublet whereas that of UCP2 is unique. The size of the messengers, compared with an RNA ladder, are 1.4 and 1.8 kb for UCP, 1.7 kb for UCP2 and 2.5 and 2.8 kb for UCP3.

The results thus show that the tissue distribution of UCP2 and UCP3 in man is very different from that of UCP: the expression of UCP2 is ubiquitous and that of UCP3 is highly specific to skeletal muscle.

What is claimed is:

1. An isolated DNA fragment comprising the nucleotide sequence of SEQ ID NO:5.
2. A vector comprising the DNA sequence of SEQ ID NO:5.
3. The recombinant DNA molecule of SEQ ID NO:5 deposited with the ATCC as ATCC NO 209000.
4. An isolated DNA fragment wherein said DNA fragment encodes UCP3s of SEQ ID NO:6.
5. The DNA fragment of claim 4 which originates from human skeletal muscle.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Unknown
<220> FEATURE:
<223> OTHER INFORMATION: Description of Unknown Organism:
       Oligonucleotide Primer DNA (UCPRF)

<400> SEQUENCE: 1
ctggacaccg ccaaagtccg                                                    20

<210> SEQ ID NO 2
<211> LENGTH: 24
<212> TYPE: DNA
<213> ORGANISM: Unknown
<220> FEATURE:
<223> OTHER INFORMATION: Description of Unknown Organism:
       Oligonucleotide Primer DNA (UCPRR)

<400> SEQUENCE: 2
agcacacaaa catgatgacg ttcc                                               24

<210> SEQ ID NO 3
<211> LENGTH: 1231
<212> TYPE: DNA
<213> ORGANISM: Unknown
<220> FEATURE:
<223> OTHER INFORMATION: Description of Unknown Organism: cDNA from
       clone UCP3L

<400> SEQUENCE: 3
tcctgggatg gagccctagg gagcccctgt gctgccctg ccgtggcagg actcacagcc          60
ccaccgctgc actgaagccc agggctgtgg agcagcctct ctccttggac ctcctctcgg       120
ccctaaaggg actgggcaga gccttccagg actatggttg gactgaagcc ttcagacgtg       180
cctcccacca tggctgtgaa gttcctgggg gcaggcacag cagcctgttt tgctgacctc       240
gttacctttc cactggacac agccaaggtc cgcctgcaga tccagggggga gaaccaggcg      300 gtccagacgg cccggctcgt gcagtaccgt ggcgtgctgg gcaccatcct gaccatggtg       360
cggactgagg gtccctgcag ccctacaat gggctggtgg ccggcctgca gcgccagatg        420
agcttcgcct ccatccgcat cggcctctat gactccgtca gcaggtgta cacccccaaa       480 ggcgcggaca actccagcct cactacccgg attttggccg gctgcaccac aggagccatg      540
gcggtgacct gtgcccagcc cacagatgtg gtgaaggtcc gatttcaggc cagcatacac      600
ctcgggccat ccaggagcga cagaaaatac agcgggacta tggacgccta cagaaccatc      660
gccagggagg aaggagtcag gggcctgtgg aaaggaactt tgcccaacat catgaggaat     720
gctatcgtca actgtgctga ggtggtgacc tacgacatcc tcaaggagaa gctgctggac      780
taccacctgc tcactgacaa cttccccctgc cactttgtct ctgcctttgg agccggcttc    840
tgtgccacag tggtggcctc cccggtggac gtggtgaaga cccggtatat gaactcacct     900
ccaggccagt acttcagccc cctcgactgt atgataaaga tggtggccca ggagggcccc    960
acagccttct acaagggatt tacaccctcc tttttgcgtt tgggatcctg gaacgtggtg   1020
atgttcgtaa cctatgagca gctgaaacgg gccctgatga aagtccagat gttacgggaa   1080
tcaccgtttt gaacaagaca agaaggccac tggtagctaa cgtgtccgaa accagttaag  1140

```
aatggaagaa aacggtgcat ccacgcacac atggacacag acccacacat gtttacagaa    1200
ctgttgttta cttgttgctg attcaagaaa c                                   1231
```

<210> SEQ ID NO 4
<211> LENGTH: 312
<212> TYPE: PRT
<213> ORGANISM: Unknown
<220> FEATURE:
<223> OTHER INFORMATION: Description of Unknown Organism: Protein UCP3L

<400> SEQUENCE: 4

```
Met Val Gly Leu Lys Pro Ser Asp Val Pro Thr Met Ala Val Lys
  1               5                  10                  15

Phe Leu Gly Ala Gly Thr Ala Ala Cys Phe Ala Asp Leu Val Thr Phe
                 20                  25                  30

Pro Leu Asp Thr Ala Lys Val Arg Leu Gln Ile Gln Gly Glu Asn Gln
             35                  40                  45

Ala Val Gln Thr Ala Arg Leu Val Gln Tyr Arg Gly Val Leu Gly Thr
         50                  55                  60

Ile Leu Thr Met Val Arg Thr Glu Gly Pro Cys Ser Pro Tyr Asn Gly
 65                  70                  75                  80

Leu Val Ala Gly Leu Gln Arg Gln Met Ser Phe Ala Ser Ile Arg Ile
                 85                  90                  95

Gly Leu Tyr Asp Ser Val Lys Gln Val Tyr Thr Pro Lys Gly Ala Asp
                100                 105                 110

Asn Ser Ser Leu Thr Thr Arg Ile Leu Ala Gly Cys Thr Thr Gly Ala
                115                 120                 125

Met Ala Val Thr Cys Ala Gln Pro Thr Asp Val Val Lys Val Arg Phe
            130                 135                 140

Gln Ala Ser Ile His Leu Gly Pro Ser Arg Ser Asp Arg Lys Tyr Ser
145                 150                 155                 160

Gly Thr Met Asp Ala Tyr Arg Thr Ile Ala Arg Glu Glu Gly Val Arg
                165                 170                 175

Gly Leu Trp Lys Gly Thr Leu Pro Asn Ile Met Arg Asn Ala Ile Val
                180                 185                 190

Asn Cys Ala Glu Val Val Thr Tyr Asp Ile Leu Lys Glu Lys Leu Leu
            195                 200                 205

Asp Tyr His Leu Leu Thr Asp Asn Phe Pro Cys His Phe Val Ser Ala
        210                 215                 220

Phe Gly Ala Gly Phe Cys Ala Thr Val Val Ala Ser Pro Val Asp Val
225                 230                 235                 240

Val Lys Thr Arg Tyr Met Asn Ser Pro Pro Gly Gln Tyr Phe Ser Pro
                245                 250                 255

Leu Asp Cys Met Ile Lys Met Val Ala Gln Glu Gly Pro Thr Ala Phe
                260                 265                 270

Tyr Lys Gly Phe Thr Pro Ser Phe Leu Arg Leu Gly Ser Trp Asn Val
            275                 280                 285

Val Met Phe Val Thr Tyr Glu Gln Leu Lys Arg Ala Leu Met Lys Val
        290                 295                 300

Gln Met Leu Arg Glu Ser Pro Phe
305                 310
```

<210> SEQ ID NO 5
<211> LENGTH: 1132
<212> TYPE: DNA
<213> ORGANISM: Unknown

-continued

```
<220> FEATURE:
<223> OTHER INFORMATION: Description of Unknown Organism: cDNA from
      clone UCP3S

<400> SEQUENCE: 5
tcctgggatg gagccctagg gagcccctgt gctgcccctg ccgtggcagg actcacagcc      60
ccaccgctgc actgaagccc aggctgtgg agcagcctct ctccttggac ctcctctcgg     120
ccctaaaggg actgggcaga gccttccagg actatggttg gactgaagcc ttcagacgtg    180
cctcccacca tggctgtgaa gttcctgggg gcaggcacag cagcctgttt tgctgacctc    240
gttacctttc cactggacac agccaaggtc cgcctgcaga tccaggggga gaaccaggcg    300
gtccagacgg cccggctcgt gcagtaccgt ggcgtgctgg gcaccatcct gaccatggtg    360
cggactgagg gtccctgcag ccctacaat gggctggtgg ccggcctgca gcgccagatg     420
agcttcgcct ccatccgcat cggcctctat gactccgtca gcaggtgta caccccccaaa    480 ggcgcggaca actccagcct cactacccgg attttggccg gctgcaccac aggagccatg    540
gcggtgacct gtgcccagcc cacagatgtg gtgaaggtcc gatttcaggc cagcatacac    600
ctcgggccat ccaggagcga cagaaaatac agcgggacta tggacgccta cagaaccatc    660 gccaggagg aaggagtcag gggcctgtgg aaaggaactt tgcccaacat catgaggaat    720
gctatcgtca actgtgctga ggtggtgacc tacgacatcc tcaaggagaa gctgctggac    780
taccacctgc tcactgacaa cttccctgc cactttgtct ctgcctttgg agccggcttc     840
tgtgccacag tggtggcctc cccggtgac gtggtgaaga cccggtatat gaactcacct     900
ccaggccagt acttcagccc cctcgactgt atgataaaga tggtggccca ggagggcccc    960
acagccttct acaagggggtg agcctcctcc tgcctccagc actccctccc agagaacagg   1020
ggcttctttc ttttcgaatg tggctaccgt gggtcaacct gggatgtagc ggtgaagagt   1080
acagatgtaa atgccacaaa gaagaagttt aaaaaaccat gcaaaaaaaa aa           1132

<210> SEQ ID NO 6
<211> LENGTH: 275
<212> TYPE: PRT
<213> ORGANISM: Unknown
<220> FEATURE:
<223> OTHER INFORMATION: Description of Unknown Organism: Protein UCP3S

<400> SEQUENCE: 6

Met Val Gly Leu Lys Pro Ser Asp Val Pro Thr Met Ala Val Lys
  1               5                  10                  15

Phe Leu Gly Ala Gly Thr Ala Ala Cys Phe Ala Asp Leu Val Thr Phe
                 20                  25                  30

Pro Leu Asp Thr Ala Lys Val Arg Leu Gln Ile Gln Gly Glu Asn Gln
             35                  40                  45

Ala Val Gln Thr Ala Arg Leu Val Gln Tyr Arg Gly Val Leu Gly Thr
         50                  55                  60

Ile Leu Thr Met Val Arg Thr Glu Gly Pro Cys Ser Pro Tyr Asn Gly
 65                  70                  75                  80

Leu Val Ala Gly Leu Gln Arg Gln Met Ser Phe Ala Ser Ile Arg Ile
                 85                  90                  95

Gly Leu Tyr Asp Ser Val Lys Gln Val Tyr Thr Pro Lys Gly Ala Asp
                100                 105                 110

Asn Ser Ser Leu Thr Thr Arg Ile Leu Ala Gly Cys Thr Thr Gly Ala
            115                 120                 125

Met Ala Val Thr Cys Ala Gln Pro Thr Asp Val Val Lys Val Arg Phe
```

-continued

```
            130                 135                 140
Gln Ala Ser Ile His Leu Gly Pro Ser Arg Ser Asp Arg Lys Tyr Ser
145                 150                 155                 160

Gly Thr Met Asp Ala Tyr Arg Thr Ile Ala Arg Glu Glu Gly Val Arg
                165                 170                 175

Gly Leu Trp Lys Gly Thr Leu Pro Asn Ile Met Arg Asn Ala Ile Val
                180                 185                 190

Asn Cys Ala Glu Val Val Thr Tyr Asp Ile Leu Lys Glu Lys Leu Leu
            195                 200                 205

Asp Tyr His Leu Leu Thr Asp Asn Phe Pro Cys His Phe Val Ser Ala
        210                 215                 220

Phe Gly Ala Gly Phe Cys Ala Thr Val Val Ala Ser Pro Val Asp Val
225                 230                 235                 240

Val Lys Thr Arg Tyr Met Asn Ser Pro Pro Gly Gln Tyr Phe Ser Pro
                245                 250                 255

Leu Asp Cys Met Ile Lys Met Val Ala Gln Glu Gly Pro Thr Ala Phe
                260                 265                 270

Tyr Lys Gly
        275
```